US010004670B2

(12) United States Patent
Köpsel

(10) Patent No.: US 10,004,670 B2
(45) Date of Patent: *Jun. 26, 2018

(54) READY-TO-USE, STABLE EMULSION

(71) Applicant: BASF SE, Ludwigshafen (DE)

(72) Inventor: Christian Köpsel, Weinheim (DE)

(73) Assignee: BASF SE, Ludwigshafen am Rhein (DE)

(*) Notice: Subject to any disclaimer, the term of this patent is extended or adjusted under 35 U.S.C. 154(b) by 0 days. days.

This patent is subject to a terminal disclaimer.

(21) Appl. No.: 15/168,315

(22) Filed: May 31, 2016

(65) Prior Publication Data

US 2016/0287491 A1    Oct. 6, 2016

Related U.S. Application Data

(63) Continuation of application No. 13/121,962, filed as application No. PCT/EP2009/062768 on Oct. 1, 2009, now Pat. No. 9,375,387.

(30) Foreign Application Priority Data

Oct. 7, 2008  (EP) ..................................... 08165989

(51) Int. Cl.

| | | |
|---|---|---|
| *A61K 8/06* | (2006.01) | |
| *A23L 33/15* | (2016.01) | |
| *A61K 8/67* | (2006.01) | |
| *A61K 47/36* | (2006.01) | |
| *A61K 47/10* | (2017.01) | |
| *A23D 7/005* | (2006.01) | |
| *A23D 7/01* | (2006.01) | |
| *A23L 2/38* | (2006.01) | |
| *A23L 2/52* | (2006.01) | |
| *A61K 8/31* | (2006.01) | |
| *A61K 8/34* | (2006.01) | |
| *A61K 8/73* | (2006.01) | |
| *A61Q 19/00* | (2006.01) | |
| *A23K 20/174* | (2016.01) | |
| *A23K 20/158* | (2016.01) | |
| *A23L 33/10* | (2016.01) | |
| *A23L 33/105* | (2016.01) | |
| *A61K 9/107* | (2006.01) | |
| *A61K 31/015* | (2006.01) | |

(52) U.S. Cl.
CPC ............ *A61K 8/062* (2013.01); *A23D 7/0053* (2013.01); *A23D 7/011* (2013.01); *A23K 20/158* (2016.05); *A23K 20/174* (2016.05); *A23L 2/38* (2013.01); *A23L 2/52* (2013.01); *A23L 33/10* (2016.08); *A23L 33/105* (2016.08); *A23L 33/15* (2016.08); *A61K 8/06* (2013.01); *A61K 8/31* (2013.01); *A61K 8/345* (2013.01); *A61K 8/67* (2013.01); *A61K 8/732* (2013.01); *A61K 9/107* (2013.01); *A61K 31/015* (2013.01); *A61K 47/10* (2013.01); *A61K 47/36* (2013.01); *A61Q 19/00* (2013.01); *A23V 2002/00* (2013.01); *A61K 2800/10* (2013.01); *A61K 2800/21* (2013.01)

(58) Field of Classification Search
None
See application file for complete search history.

(56) References Cited

U.S. PATENT DOCUMENTS

| | | |
|---|---|---|
| 3,110,598 A | 11/1963 | Mueller et al. |
| 4,522,743 A | 6/1985 | Horn et al. |
| 4,844,934 A | 7/1989 | Lueddecke et al. |
| 5,028,625 A | 7/1991 | Motola et al. |
| 5,078,980 A | 1/1992 | Mullner et al. |
| 5,350,773 A | 9/1994 | Schweikert et al. |
| 5,364,563 A | 11/1994 | Cathrein et al. |
| 5,637,618 A | 6/1997 | Kurtz et al. |
| 5,827,539 A | 10/1998 | Gellenbeck |
| 5,863,953 A | 1/1999 | Luddecke et al. |
| 5,891,907 A | 4/1999 | Kolter et al. |
| 5,968,251 A | 10/1999 | Auweter et al. |
| 6,132,790 A | 10/2000 | Schlipalius |
| 6,201,155 B1 | 3/2001 | Burdet et al. |
| 6,235,315 B1 | 5/2001 | Runge et al. |
| 6,287,615 B1 | 9/2001 | Runge et al. |
| 6,639,113 B2 | 10/2003 | Runge et al. |
| 7,070,812 B2 | 7/2006 | Runge et al. |
| 2002/0110599 A1 | 8/2002 | Auweter et al. |
| 2002/0128325 A1 | 9/2002 | Runge et al. |
| 2002/0188019 A1 | 12/2002 | Ley et al. |
| 2003/0125310 A1 | 7/2003 | Hahnlein et al. |
| 2004/0033246 A1 | 2/2004 | Naru et al. |
| 2005/0079223 A1 | 4/2005 | Estrella De Castro et al. |
| 2005/0084462 A1 | 4/2005 | Klingenberg |
| 2005/0227906 A1 | 10/2005 | Schudel et al. |
| 2006/0035871 A1 | 2/2006 | Auweter et al. |
| 2008/0026124 A1 | 1/2008 | Musaeus et al. |
| 2008/0113076 A1 | 5/2008 | Klingenberg |
| 2008/0131515 A1 | 6/2008 | Ogawa et al. |
| 2008/0193539 A1 | 8/2008 | Voelker |
| 2008/0207775 A1 | 8/2008 | Musaeus et al. |
| 2010/0028444 A1 | 2/2010 | Matuschek et al. |
| 2010/0041607 A1 | 2/2010 | Jensen et al. |
| 2010/0047426 A1 | 2/2010 | Matuschek et al. |
| 2010/0120922 A1 | 5/2010 | Kopsel et al. |
| 2010/0267838 A1 | 10/2010 | Köpsel |
| 2011/0207831 A1 | 8/2011 | Köpsel |

FOREIGN PATENT DOCUMENTS

| | | |
|---|---|---|
| CH | 418106 A | 7/1966 |
| CN | 101378668 A | 3/2009 |

(Continued)

OTHER PUBLICATIONS

Manz, "Die anwendung und bedeutung von synthetischen carotinoiden in der lebens- und futtermittel-sowie in der pharmazeutischen industrie," Chimia, 1967, vol. 21, pp. 329-335. (see US-2010/0267838-A1).

(Continued)

*Primary Examiner* — Bong-Sook Baek
(74) *Attorney, Agent, or Firm* — Drinker Biddle & Reath LLP

(57) ABSTRACT

The present invention relates to a stable emulsion, ready for use, of fat-soluble vitamins or carotenoids, a process for the preparation thereof, and the use thereof as addition to animal feeds, human foods and dietary supplements, and cosmetic and pharmaceutical compositions.

8 Claims, No Drawings

(56) References Cited

FOREIGN PATENT DOCUMENTS

| | | |
|---|---|---|
| DE | 1211911 B | 3/1966 |
| DE | 3119383 A1 | 12/1982 |
| DE | 10059213 A1 | 6/2002 |
| DE | 10122898 A1 | 11/2002 |
| DE | 102004046026 A1 | 3/2006 |
| DE | 102005030952 A1 | 1/2007 |
| EP | 0 065 193 A2 | 11/1982 |
| EP | 0 239 086 A2 | 9/1987 |
| EP | 0410236 A2 | 1/1991 |
| EP | 0416236 A2 | 3/1991 |
| EP | 0 551 638 A1 | 7/1993 |
| EP | 0732064 A1 | 9/1996 |
| EP | 0800825 A1 | 10/1997 |
| EP | 0832569 A2 | 4/1998 |
| EP | 0848913 A2 | 6/1998 |
| EP | 0937412 A1 | 8/1999 |
| EP | 0978508 A2 | 2/2000 |
| EP | 1 213 013 A2 | 6/2002 |
| EP | 1219292 A1 | 7/2002 |
| EP | 1228705 A2 | 8/2002 |
| EP | 1 258 200 A2 | 11/2002 |
| EP | 1460060 A1 | 9/2004 |
| EP | 1 875 814 A1 | 1/2008 |
| EP | 1 927 287 A1 | 6/2008 |
| EP | 1952845 A1 | 8/2008 |
| GB | 885677 A | 12/1961 |
| GB | 970363 A | 9/1964 |
| JP | 63137657 A | 6/1988 |
| JP | 2025428 A | 1/1990 |
| JP | 4-262758 A | 9/1992 |
| JP | 7-99924 | 4/1995 |
| JP | 7-083684 B2 | 9/1995 |
| JP | 7083684 B | 9/1995 |
| JP | 2001226293 A | 8/2001 |
| JP | 2004-196673 A | 7/2004 |
| JP | 2007520603 A | 7/2007 |
| WO | WO-91/06292 A1 | 5/1991 |
| WO | WO-93/04598 A1 | 3/1993 |
| WO | WO-94/19411 A1 | 9/1994 |
| WO | WO-96/13178 A1 | 5/1996 |
| WO | WO-96/23420 A1 | 8/1996 |
| WO | WO-03/066583 A1 | 8/2003 |
| WO | WO-03/086293 A2 | 10/2003 |
| WO | WO-03/102116 A2 | 12/2003 |
| WO | WO-2005/060923 A1 | 7/2005 |
| WO | WO 2005/075066 | 8/2005 |
| WO | WO-2006/125591 A1 | 11/2006 |
| WO | WO-2007/003543 A1 | 1/2007 |
| WO | WO-2007/009601 A1 | 1/2007 |
| WO | WO-2007/020057 A1 | 2/2007 |
| WO | WO-2007/045488 A1 | 4/2007 |
| WO | WO-2007/090610 A2 | 8/2007 |
| WO | WO-2008/087090 A1 | 7/2008 |
| WO | WO-2008/087139 A1 | 7/2008 |
| WO | WO-2008/087140 A2 | 7/2008 |
| WO | WO-2009/027499 A2 | 3/2009 |
| WO | WO-2009/068432 A1 | 6/2009 |
| WO | WO-2010/040683 A1 | 4/2010 |

OTHER PUBLICATIONS

International Preliminary Report on Patentability for PCT/EP2009/062768, dated Apr. 21, 2011 (See English translation).
International Search Report, PCT/EP2009/062768, dated Jan. 6, 2010.

READY-TO-USE, STABLE EMULSION

CROSS-REFERENCE TO RELATED APPLICATIONS

This application is a continuation of Ser. No. 13/121,962, filed May 4, 2011, which is incorporated by reference. Application Ser. No. 13/121,962 is a national stage application (under 35 U.S.C. § 371) of PCT/EP2009/62768, filed Oct. 1, 2009, which claims benefit of European application 08 165989.8, filed Oct. 7, 2008. All of which are incorporated herein by reference in their entirety.

DESCRIPTION

The present invention relates to a stable emulsion, ready for use, of fat-soluble vitamins or carotenoids, a process for the preparation thereof, and the use thereof as addition to animal feeds, human foods and dietary supplements, and cosmetic and pharmaceutical compositions.

The fat-soluble vitamins A, D, E or K, and the derivatives thereof, and the carotenoids such as, for example, canthaxanthin, astaxanthin, zeaxanthin, lutein, lycopene or β-carotene are often employed not directly as pure substances in the animal feed and human food industries, the cosmetic industry and the pharmaceutical industry. On the contrary, formulations of these fat-soluble substances are used, thus making it possible to disperse the fat-soluble substances homogeneously in finely dispersed form in a water-containing medium. Both solid and liquid formulations of these fat-soluble substances are employed commercially, depending on the area of application.

Whereas vitamins A, D or K are ordinarily employed in the living organism, because of their physiological effect, vitamin E is frequently also used as antioxidant in various applications in vitro. Carotenoids, which likewise have an antioxidant effect, are employed as colorants in many applications and, in this case, can simultaneously fulfill a physiological function. β-Carotene for example is colorant and provitamin A.

In the beverage industry, additives are ordinarily added in the form of liquid concentrates to the beverages. In the case of water-soluble, powdered formulations, normally aqueous dispersions are initially prepared from these powders in the production process. In the case of liquid formulations such as, for example, emulsions, this process step is unnecessary.

EP 0 239 086 describes emulsions of a carotenoid which is dissolved in oil, where the oil droplets are stabilized by employing a mixture of an ester of a long-chain fatty acid with ascorbic acid and a cold water-soluble starch product such as, for example, starch octenyl succinate. The carotenoid concentration in these emulsions is between 0.1 and 2%.

In EP 0 551 638, stable liquid emulsions of fat-soluble vitamins or carotenoids are prepared, the continuous phase being glycerol or a glycerol-water mixture, and employing as emulsifier and stabilizer an ester of ascorbic acid with long-chain fatty acids. In the case of β-carotene, the products are notable for a brilliant yellow hue.

The emulsions, disclosed in the prior art, of fat-soluble active substances which comprise the emulsifier ascorbyl palmitate are as yet unsatisfactory for use in mineral-rich sports drinks or on use of drinking water with a high content of calcium or magnesium ions, because formation of a ring is observed in the beverage bottles, indicating instability of the emulsion employed.

The present invention was based on the object of providing a stable emulsion ready for use, which both exhibits good storage stability in relation to microbiological attack, and is thermally insensitive and in particular shows improved stability on use in calcium- or magnesium-containing beverages or on use of drinking water with a high content of calcium or magnesium ions.

This object is achieved by a stable emulsion ready for use, comprising
a) a dispersed oil phase which comprises a fat-soluble vitamin or a carotenoid,
and
b) an aqueous phase which comprises a physiologically tolerated polyalcohol and a chemically modified starch as water-soluble protective colloid,
in which the content of fat-soluble vitamin or of carotenoid is at least 2% by weight, and the content of a further substance with an emulsifying effect besides the chemically modified starch is less than 2% by weight, where the % by weight data are in each case based on the total weight of the emulsion.

The content of the fat-soluble vitamin or of the carotenoid in the stable emulsion ready for use according to the invention is at least 2% by weight, preferably 3 to 30% by weight, particularly preferably 3 to 12% by weight, in particular 3 to 6% by weight, where the % by weight data are based on the total weight of the emulsion.

The content of a further substance with an emulsifying effect besides the chemically modified starch in the stable emulsion ready for use according to the invention is less than 2% by weight, preferably less than 1% by weight. If the further substance with an emulsifying effect is ascorbyl palmitate, the content of ascorbyl palmitate is preferably less than 0.5% by weight, particularly preferably less than 0.25% by weight, especially less than 0.1% by weight, where the % by weight data are based on the total weight of the emulsion.

The fat-soluble vitamin may be for example vitamins A, D, E or K or a derivative thereof. The stable emulsion ready for use according to the invention preferably comprises a carotenoid such as, for example, canthaxanthin, astaxanthin, zeaxanthin, lutein, lycopene or β-carotene. Preferred carotenoids are lycopene or β-carotene, especially β-carotene.

The stable emulsion ready for use according to the invention preferably comprises a dispersed oil phase which comprises a carotenoid, preferably lycopene or β-carotene, especially β-carotene, dissolved in a physiologically tolerated oil.

Suitable physiologically tolerated oils are in principle oils of synthetic, mineral, vegetable or animal origin. Examples are sesame oil, corn oil, cottonseed oil, soybean oil, peanut oil, esters of medium-chain vegetable fatty acids, oleostearin, liquid paraffin, glyceryl stearate, isopropyl myristate, diisopropyl adipate, cetylstearyl 2-ethyl-hexanoate, hydrogenated polyisobutene, caprylic acid/capric acid triglycerides, palm oil, palm kernel oil, lanolin and PUFAs (polyunsaturated fatty acids) such as eicosapentaenoic acid (EPA), docosahexaenoic acid (DHA) and alpha-linolenic acids.

Physiologically tolerated oils of vegetable or animal origin which are liquid at 30° C. are preferred, such as sunflower oil, palm oil, palm kernel oil, sesame oil, corn oil, cottonseed oil, soybean oil, peanut oil, esters of medium-chain triglycerides (so-called MCT oils), fish oils such as mackerel, sprat or salmon oil. Physiologically tolerated oils of vegetable origin which comprise as far as possible only saturated fatty acids are particularly preferred, such as, for example, palm kernel oil or coconut oil, especially the esters of medium-chain triglycerides obtainable therefrom.

The stable emulsion ready for use according to the invention comprises an aqueous phase which comprises a physiologically tolerated polyalcohol and a chemically modified starch as water-soluble protective colloid. The content of the physiologically tolerated polyalcohol is preferably from 10 to 60% by weight, particularly preferably from 30 to 55% by weight, based on the total weight of the emulsion.

The physiologically tolerated polyalcohol is preferably glycerol, monoesters of glycerol with $C_1$-$C_5$ monocarboxylic acids, monoethers of glycerol or sorbitol. Glycerol is particularly preferred as physiologically tolerated polyalcohol.

The content of the chemically modified starch in the stable emulsion ready for use according to the invention is preferably from 5 to 40% by weight, in particular 10 to 25% by weight, based on the total weight of the emulsion.

Chemically modified starch means chemically and/or enzymatically prepared starch transformation products. Possibilities in this connection are starch ethers, starch esters or starch phosphates. Preferred representatives from this group are starch esters, especially octenyl succinate starch such as, for example, Capsul® (sodiumoctenyl succinate starch) from National Starch, Cleargum CO 01 from Roquette or Purity® Gum 2000 (sodium octenylsuccinate starch) from National Starch, especially a sodium octenylsuccinate starch such as Purity® Gum 2000.

The content of the dispersed oil phase in the stable emulsion ready for use according to the invention is preferably from 10 to 40% by weight, in particular 10 to 30% by weight, based on the total weight of the emulsion.

A preferred stable emulsion ready for use according to the invention has a dispersed oil phase which more than 90% by weight, in particular more than 95% by weight, consists of a carotenoid and a physiologically tolerated oil.

To increase the stability of the active substance toward oxidative degradation it is advantageous for the emulsion to comprise stabilizers such as α-tocopherol, t-butylhydroxytoluene, t-butylhydroxyanisole, ascorbic acid or ethoxyquin, especially α-tocopherol.

A particularly preferred stable emulsion ready for use according to the invention is one where the dispersed oil phase comprises from 3 to 6% by weight of β-carotene and from 7 to 20% by weight of a medium-chain triglyceride, the aqueous phase comprises from 10 to 25% by weight of starch sodium octenyl succinate and from 30 to 55% by weight of glycerol, and the ascorbyl palmitate content in the emulsion is less than 0.5% by weight, preferably less than 0.25% by weight, in particular less than 0.1% by weight, where the % by weight data are based in each case on the total weight of the emulsion.

The dispersed oil phase in the stable emulsion ready for use according to the invention is present in the form of small oil droplets in the continuous aqueous phase.

The particle size of the droplets of the dispersed oil phase may generally extend from 100 nm to 100 μm. The droplets of the dispersed oil phase preferably have an average particle size of from 250 to 500 nm.

The statement of the average particle size refers to the volume-weighted average diameter (see handbook for Malvern Mastersizer S, Malvern Instruments Ltd., UK), which can be determined by Fraunhofer diffraction.

Besides the chemically modified starch, it is possible for the stable emulsions ready for use according to the invention to comprise further protective colloids. The following substances are suitable for this purpose, for example:

ox, pig or fish gelatin, especially acid- or base-degraded gelatin with Bloom numbers in the range from 0 to 250, very particularly preferably gelatin A 100, A 200, A 240, B 100 and B 200, and low molecular weight, enzymatically degraded gelatin types with Bloom numbers 0 and molecular weights of from 15 000 to 25 000 D, such as, for example, Collagel A and Gelitasol P (from Stoess, Eberbach), and mixtures of these gelatin types.

Starch, dextrin, pectin, gum arabic (gum acacia), ligninsulfonates, chitosan, poly-styrenesulfonate, alginates, casein, caseinate, methylcellulose, carboxymethyl-cellulose, hydroxypropylcellulose or mixtures of these protective colloids.

Vegetable proteins such as soybean, rice and/or wheat proteins, it being possible for these vegetable proteins to be present partly degraded or in undegraded form.

The invention further relates also to a process for preparing a stable emulsion ready for use, comprising a) a dispersed oil phase which comprises a fat-soluble vitamin or a carotenoid, and b) an aqueous phase which comprises a physiologically tolerated polyalcohol and a chemically modified starch as water-soluble protective colloid, in which the content of fat-soluble vitamin or of carotenoid is at least 2% by weight, and the content of a further substance with an emulsifying effect besides the chemically modified starch is less than 2% by weight, where the % by weight data are in each case based on the total weight of the emulsion, where an oil phase which comprises a fat-soluble vitamin or a carotenoid and an aqueous phase which comprises a physiologically tolerated polyalcohol and a chemically modified starch as water-soluble protective colloid are emulsified together, and subsequently the emulsion is homogenized under elevated pressure.

Preferred embodiments in relation to the components of the dispersed oil phase and of the aqueous phase, and the amounts thereof used are to be found in the explanations given at the outset.

The stable emulsion ready for use according to the invention is distinguished inter alia by itself having good storage stability. It is moreover possible to incorporate the emulsion of the invention without difficulty into calcium- or magnesium-containing sports drinks or into beverages which comprise drinking water with a high content of calcium or magnesium ions, with the produced beverages exhibiting good stability in relation to an unwanted ring formation.

The stable emulsion ready for use according to the invention is suitable inter alia as additive to human food preparations, for example for coloring food products such as beverages, as composition for producing pharmaceutical and cosmetic preparations, and for the production of dietary supplement products, for example of multivitamin products in the human and animal sectors. The stable emulsion ready for use is preferably suitable as addition to beverages.

The present invention therefore further also relates to the use of the stable emulsion ready for use according to the invention described above as addition to animal feeds, human foods, dietary supplements and cosmetic and pharmaceutical compositions, in particular as addition to beverages.

The present invention likewise relates to animal feeds, human foods and dietary supplements, in particular a beverage which comprises the stable emulsion ready for use according to the invention.

The invention is explained by the following examples which do not, however, restrict the invention:

EXAMPLES

Example 1

145 g of water and 200 g of glycerol were mixed in a 1 l glass beaker and heated to 60° C. 93 g of modified starch (Purity Gum 2000 from National Starch) were added to this mixture. The mixture was left to swell at 60° C. for 60 minutes.

65.5 g of β-carotene dispersion (Lucarotin 33 MCT, BASF, 33% by weight of β-carotene) in a 250 ml three-necked flask were heated in an oil bath heated to 180° C. until the β-carotene was completely dissolved. The oil phase was then introduced into the aqueous phase while agitating with a tooth-ringed disperser (Ultra Turrax) at 10 000 rpm. After an emulsifying time of 15 minutes, the emulsion was finely emulsified using a high-pressure homogenizer at 700 bar. A water-dispersible emulsion with 4% by weight of β-carotene was obtained. When dispersed in water, the β-carotene-oil droplets had an average particle size of 275 nm.

The invention claimed is:

1. A stable emulsion ready for use, comprising
   a) a dispersed oil phase which comprises from 2 to 6% by weight of a carotenoid completely dissolved in 7 to 20% by weight of a medium-chain triglyceride, wherein the carotenoid is selected from the group consisting of canthaxanthin, astaxanthin, zeaxanthin, lutein, lycopene and β-carotene; and
   b) an aqueous phase which comprises from 30 to 55% by weight of glycerol and from 10 to 25% by weight of starch sodium octenyl succiate as water-soluble protective colloid,
   wherein the content of a further substance with an emulsifying effect besides the starch sodium octenyl succinate is less than 2% by weight, and
   wherein the % by weight data are in each case based on the total weight of the emulsion.

2. The stable emulsion ready for use according to claim 1, where the dispersed oil phase comprises more than 90% by weight of the carotenoid and the medium-chain triglyceride based on the total weight of the dispersed oil phase.

3. The stable emulsion ready for use according to claim 1 wherein the content of the carotenoid is from 3 to 6% by weight based on the total weight of the emulsion, and wherein the stable emulsion comprises less than 0.5% by weight of ascorbyl palmitate based on the total weight of the emulsion.

4. The stable emulsion ready for use according to claim 1, where the dispersed oil phase is in form of oil droplets having an average particle size of from 250 to 500 nm.

5. A process for preparing a stable emulsion ready for use according to claim 1, comprising:
   a) mixing glycerol and water and adding the starch sodium octenyl succiate to the mixture of glycerol and water to form the aqueous phase,
   b) dissolving the carotenoid in the medium-chain triglyceride by heating to form the dispersed oil phase, and
   c) introducing the dispersed oil phase to the aqueous phase, emulsifying the dispersed oil phase and the aqueous phase together to obtain an emulsion and subsequently homogenizing the emulsion.

6. A composition comprising the stable emulsion ready for use according to claim 1, wherein the composition is a cosmetic or pharmaceutical composition.

7. A composition comprising the stable emulsion ready for use according to claim 1, wherein the composition is a beverage.

8. A composition comprising the stable emulsion ready for use according to claim 1, wherein the composition is an animal feed, human food, or dietary supplement.

* * * * *